US008684974B2

(12) United States Patent
Richard

(10) Patent No.: US 8,684,974 B2
(45) Date of Patent: *Apr. 1, 2014

(54) ACCESS ASSEMBLY

(71) Applicant: Covidien LP, Mansfield, MA (US)

(72) Inventor: Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/751,553

(22) Filed: Jan. 28, 2013

(65) Prior Publication Data

US 2013/0137933 A1    May 30, 2013

Related U.S. Application Data

(63) Continuation of application No. 12/467,433, filed on May 18, 2009, now Pat. No. 8,403,889.

(60) Provisional application No. 61/075,521, filed on Jun. 25, 2008.

(51) Int. Cl.
*A61M 5/178* (2006.01)

(52) U.S. Cl.
USPC .............. 604/167.01; 604/180; 606/108

(58) Field of Classification Search
USPC ......... 604/164.01, 167.01–167.06, 174, 180; 606/108

See application file for complete search history.

(56) References Cited

U.S. PATENT DOCUMENTS

| | | | |
|---|---|---|---|
| 3,994,287 A | 11/1976 | Turp et al. | |
| 4,623,348 A | 11/1986 | Feit | |
| 4,921,479 A | 5/1990 | Grayzel | |
| 5,364,367 A | 11/1994 | Banks et al. | |
| 5,403,264 A | 4/1995 | Wohlers et al. | |
| 5,683,378 A | 11/1997 | Christy | |
| 5,752,970 A | 5/1998 | Yoon | |
| 6,045,535 A | 4/2000 | Ben Nun | |
| 6,171,282 B1 | 1/2001 | Ragsdale | |
| 6,447,489 B1 | 9/2002 | Peterson | |
| 8,403,889 B2 * | 3/2013 | Richard | 604/167.01 |
| 2002/0019610 A1 | 2/2002 | Bousquet | |
| 2003/0120261 A1 | 6/2003 | Gellman | |
| 2003/0233115 A1 | 12/2003 | Eversull | |

FOREIGN PATENT DOCUMENTS

WO    WO 84/01512 A1    4/1984

OTHER PUBLICATIONS

European Search Report for corresponding EP09251623 date of mailing is Dec. 7, 2011(7 Pgs).

* cited by examiner

*Primary Examiner* — Theodore Stigell

(57) ABSTRACT

A surgical access assembly including a base and an elongated member extending from the base. The bass defines a central axis and has an opening for receipt of a surgical instrument. The elongated member defines a passageway for passage of at least a portion of the surgical instrument and is adapted to assume a substantially rolled configuration in a normal unstressed condition thereof. When in the rolled configuration, the elongated member is rolled transverse to the central axis.

13 Claims, 6 Drawing Sheets

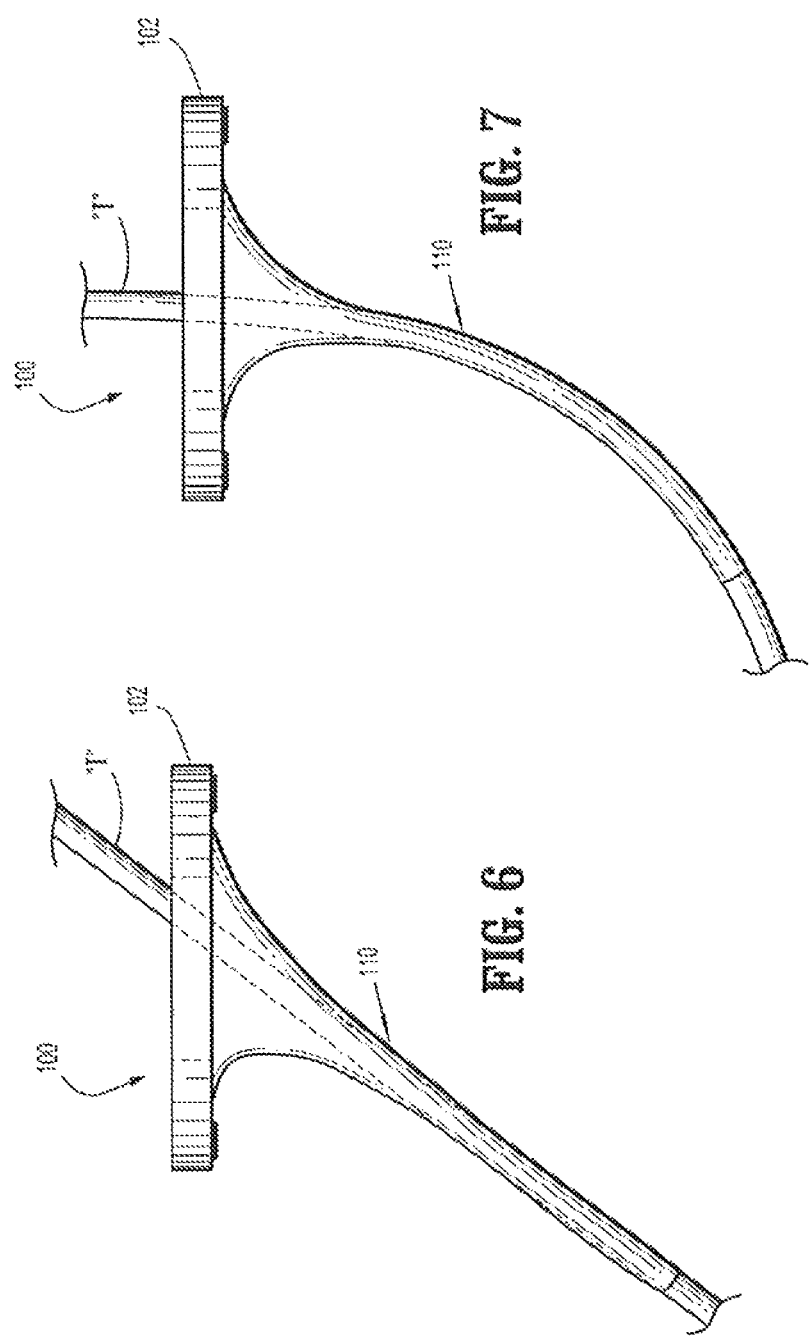

ACCESS ASSEMBLY

CROSS REFERENCE TO RELATED APPLICATIONS

The present application is a continuation application of U.S. patent application Ser. No. 12/467,433, filed on May 18, 2009, now U.S. Pat. No. 8,403,889, which claims the benefit of and priority to U.S. Provisional Patent Application Ser. No. 61/075,521, filed on Jun. 25, 2008, the entire disclosure of each application is incorporated herein by reference.

BACKGROUND

1. Technical Field

The present disclosure relates to assemblies for accessing a body cavity, and more particularly, to an access assembly having a low profile.

2. Background of Related Art

Trocar and other access assemblies are used by surgeons to operate on a patient without having to create large incisions that may become infected and may cause major scaring. Access assemblies are known in the art, as are the instruments inserted therethrough for operating within the body cavity. Typically, an access assembly includes a housing, and a tubular member or cannula affixed to the housing and configured for insertion into a body cavity. These assemblies generally include a zero closure seal mounted within the housing to prevent the escape of insufflation gas and an instrument seal also within the housing for forming a seal about the instrument.

The cannula of conventional access assemblies are limited in that they reduce the type and configuration of instruments that may be inserted into a body cavity. A curved or otherwise bent instrument may not be inserted through a conventional cannula. In addition, manipulation of the inserted instrument is limited by the dimensioning of the cannula. Even further, the housing and a conventional cannula incorporates both the instrument and zero closure seal, and, as a result, presents a relatively large profile encompassing a significantly larger area within the operative field.

Therefore, it would be beneficial to have art access assembly including a low profile housing and capable of permitting offset manipulation of the instrument.

SUMMARY

In accordance with one embodiment of the present disclosure, a surgical access assembly includes a base defining a central axis and having an opening for receipt of a surgical instrument and an elongated member extending from the base. The elongated member may define a passage for passage of the surgical instrument. The elongated member is adapted to assume a substantial rolled configuration in a normal unstressed condition thereof. The elongated member may be adapted to substantially seal the passage when in the rolled configuration thereof. As a further feature, the elongated member may be adapted to establish a substantial sealed relation with the surgical instrument received, within the passage. In one embodiment, the elongated member may include an elastomeric material which is adapted to permit angulated movement of the surgical instrument relative to the central axis. The elongated member may include a leading end portion which is substantially closed in the absence of the surgical instrument to substantially seal the passage.

The elongated member may include a coating for facilitating the insertion and removal of an endoscopic instrument, and is configured to receive endoscopic instruments of varying diameters. The elongated member may be configured to receive a endoscopic instrument having a curved length.

The base may include an adhesive ring for selectively sealing the base to a patient. In the alternative, the base may include one or more suture tie down members. The suture tie down members each may include a recess formed about the perimeter of the base. Alternatively, the suture tie down members may include labs extending from the perimeter of the base. The base may include a substantially disc-shaped member having a low profile, and may be devoid of a seal.

BRIEF DESCRIPTION OF THE DRAWINGS

The foregoing summary, as well as the following detailed description will be better understood when read in conjunction with the appended figures. For the purpose of illustrating the present disclosure, a preferred embodiment is shown. It is understood, however, that the present disclosure is not limited to the precise arrangement and instrumentalities shown.

FIG. 6 is a side view of the access assembly of FIGS. 1-5 illustrating the endoscopic instrument manipulated within the access assembly;

FIG. 7 is a side view of the access assembly of FIGS. 1-6 illustrating a curved endoscopic instrument positioned within the access assembly.

DETAILED DESCRIPTION

Figure 1:
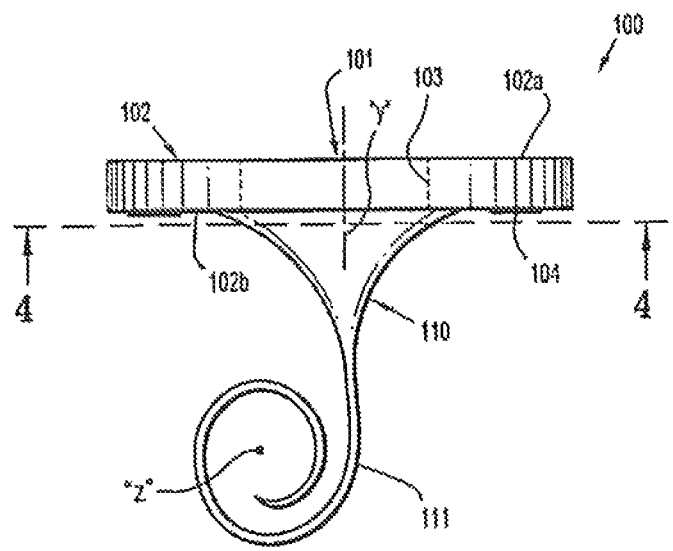
FIG. 1 is a side view of an access assembly according to aspects of the present disclosure in an initial or pre-stretched and roiled condition.

Referring now to the drawings wherein like reference numerals illustrate similar components throughout the several views. As shown in the drawings and as described throughout the following description, as is traditional, when referring to relative positioning on an object, the term "proximal" refers to the end of the apparatus which is closer to the user and the term "distal" refers to the end of the apparatus which, is further from the user.

With reference to FIGS. 1-5, an embodiment of an access assembly in accordance with the aspects of the present disclosure is shown generally as access assembly 100. Access assembly 100 includes base 102 and elongated member 110 extending from the base 102 and defining a longitudinal axis "y". Access assembly 100 defines a longitudinal passageway 101 extending through the base 102 and elongated member 310, and is adapted for receiving an endoscopic instrument.

Base 102 of access assembly 100 may define a substantially flat circular member having proximal and distal surfaces 102a, 102b. Base 102 includes opening 103 which forms part of longitudinal passageway 101. Base 102 is constructed of plastic, metal or any other suitable material. As will be discussed in further detail below, base 102 is scented to elongated member 110. Base 102 may include an adhesive ring 104 circumscribing opening 103 on distal surface 102b. Adhesive ring 104 may be adapted to selectively secure base 102 to a patient during an endoscopic procedure. Adhesive ring 104 may include any biocompatible adhesive suitable far selectively affixing base 102 to a patient. Adhesive ring 104 may form a seal between the patient and base 102 to prevent she escape of insufflation gas from within the cavity of the patient. It is envisioned, however, that distal surface 102b of base 102 may include a second ring (not shown) configured to form a seal between base 102 and the patient.

Elongated member 110 includes a flexible tapered sleeve 111 having substantially open proximal end 110a, and distal end 110b which is capable of assuming an open or closed position in the presence or absence of a surgical instrument, respectively. Tapered sleeve 111 is substantially tapered along a length thereof. Proximal end 110a is securely affixed to distal surface 102b of base 102 in any suitable manner, including, but not limited to, welding, adhesives and mechanical fasteners. Elongated member 110 is constructed from an elastomeric material that is capable of stretching to receive an endoscopic instrument therethrough, in one embodiment, elongated member 110 may include a tubular fabric coated or impregnated with an elastomeric material. This arrangement is disclosed in commonly assigned U.S. patent application Ser. No. 10/067,056, bled Oct. 15, 2004, the entire contents of which is incorporated herein by reference. Elongated member 110 may be fabricated from any material which is capable of receiving a surgical instrument "I" and radially expanding to permit passage of the surgical instrument "I" in sealed relation. Some suitable materials include medical grade polymers and metals. In an exemplary embodiment, elongated member 110 includes a braided material of inelastic filaments covered by an elastomeric membrane of, e.g., urethane, or any elastomeric material or as generally disclosed in commonly assigned U.S. Pat. Nos. 5,431,676 and 6,245,052, the entire contents of each being incorporated herein by reference. Elongated member 110 is adapted to form, a seal about the endoscopic instrument to substantially prevent the egress or release of insufflation gases or fluids about the instrument. Elongated seal member 110 may receive instruments of different and varying diameters and/or instruments having curved or bent lengths. Due to its resilient characteristics, elongated member 110 further permits greater manipulation of endoscopic instrument "I" within the elongated member 110 providing a large degree of off-axis or angulated movement of the instrument relative to conventional inflexible cannulas.

Figure 2:
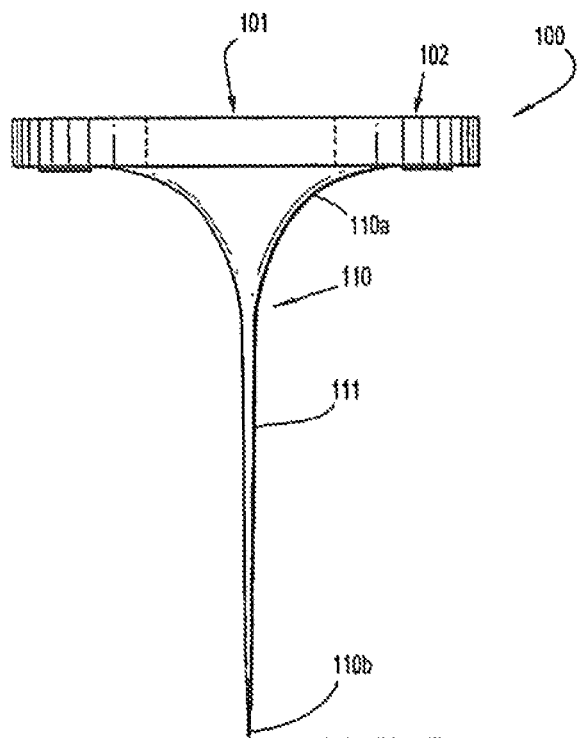
FIG. 2 is a side view of the access assembly of FIG. 1 in a stretched and extended condition.
Figure 3:
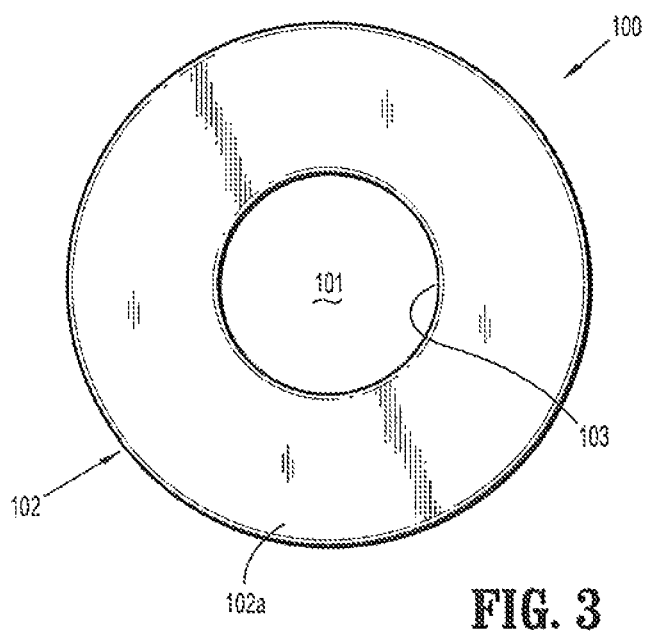
FIG. 3 is a top view of the access assembly of FIGS. 1 and 2.
Figure 4:
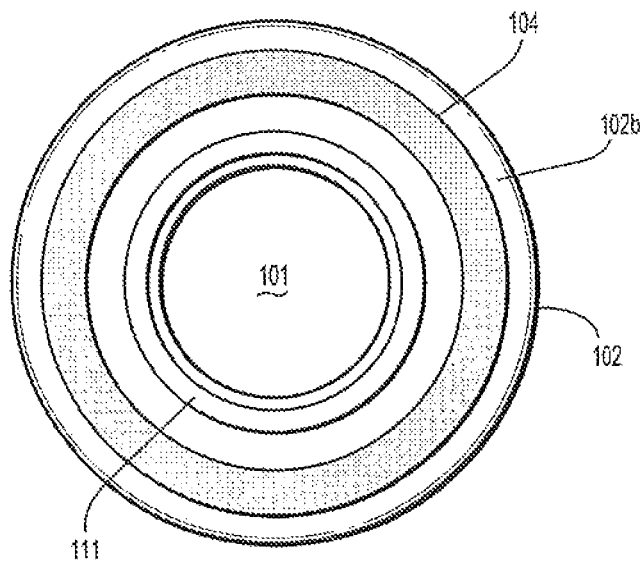
FIG. 4 is a cross-sectional view of the access assembly of FIGS. 1-3 taken along line 4-4 of FIG. 1.

With particular reference to FIG. 1, in an initial or pre-stretched condition, elongated member 110 defines a roiled or spiraled configuration about an axis "z" that is transverse to longitudinal axis "y". This arrangement may assist in establishing a seal within longitudinal passageway 101 of access member 100. In addition, distal end 110b of elongated member 110 may be adapted to form a zero closure seal, such that in the absence of an endoscopic instrument, distal end 110b is sealed. Thus, the spiraled or rolled, configuration of elongated member 110, in conjunction with the ability of distal end 110b to close, provides a substantial seal within access assembly 100 when access assembly 100 is not in use receiving an endoscopic instrument and increases the integrity of the seal defined within access assembly 100. Alternatively, distal end 110b of elongated member 110 may be partially open, whereby the roiling of elongated member 110 establishes the seal within access assembly 100. FIG. 2 illustrates elongated member 111 in the stretched or unrolled position which is assumed upon introduction of the surgical instrument. This rolled configuration may be preset during manufacture, e.g., set in the robed configuration during curing of the elastomer. In the alternative, elongated member 110 may be a shape memory material adapted to assume the rolled configuration upon exposure to a predefined temperature, e.g. body temperature. Such shape memory materials capable of performing in this manner are appreciated by one skilled in the art.

Elongated member 110 thus can serve its both the zero closure seal and the instrument seal for access assembly 100, and removes the necessity of positioning these seals within housing or base 102. As a consequence, base 102 may be reduced in height. This reduced height or profile will increase the operating area available above the patient to improve instrument maneuverability, thereby potentially facilitating completion of the surgical procedure.

Figure 5:
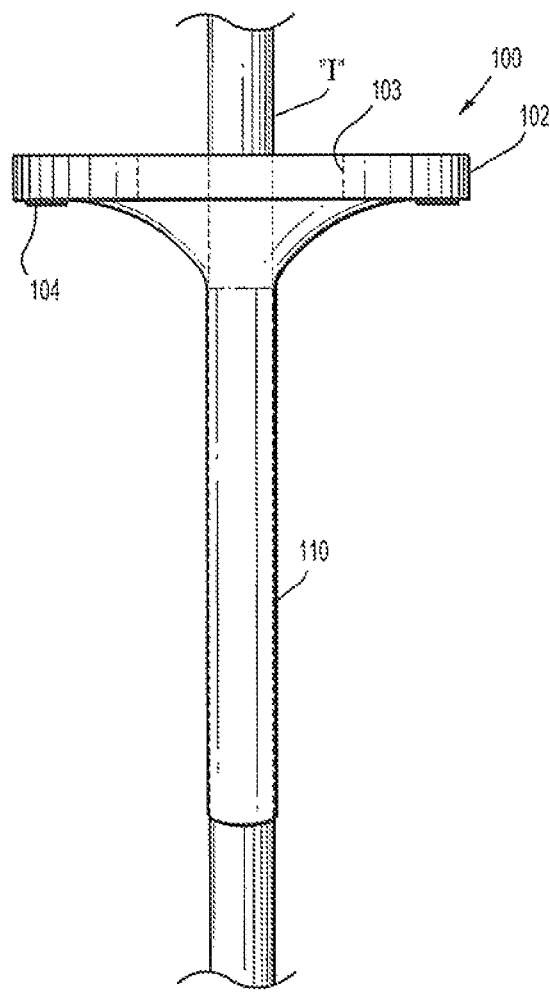
FIG. 5 is a side view of the access assembly of FIGS. 1-4 illustrating an endoscopic instrument positioned within the access assembly.

Access assembly 100 will be discussed in the terms of use of the assembly 100 in a laparoscopic surgery. The abdominal cavity is insufflated with a suitable gas, e.g., $CO_2$ gas, as is conventional and in the art. In one method, a Veress needle may be introduced within access assembly 100 and advanced through longitudinal passage 101 to cause elongated member to unroll from the condition depicted in FIG. 1 to the condition depicted in FIG. 2. Thereafter, the Veress needle with mounted access assembly 100 is advanced within the abdominal cavity. The Veress needle is flu idly coupled to a source insufflation gases to insufflate the body cavity. The Veress needle is removed leaving elongated member 110 of access assembly 100 in position accessing the body cavity. Upon removal, of the Veress needle, elongated member 110 assumes the coiled or roiled configuration of FIG. 1. In this condition, elongated member 110 is substantially sealed preventing escape of gases through access assembly 100. Thereafter, a surgical instrument is advanced through longitudinal passage 101 of access assembly 100 causing elongated member to assume the substantially linear condition of FIG. 2. Elongated member 110 establishes a seal about the instrument. FIG. 5 illustrates surgical instrument "I" positioned within access assembly 100.

Due to its elastomeric characteristics, surgical instrument may be angulated relative to longitudinal axis "y" of seat housing during performance of the procedure. The degree of angulation is significantly greater than inflexible cannula assemblies. FIG. 6 illustrates lateral offset movement of the surgical instrument. As appreciated, this tea turn permits access to tissue remote from access assembly 100 thereby potentially reducing the number of cannula assemblies required to perform the procedure. During angulation, elongated member 110 maintains a seal about the surgical instrument.

With reference now to FIGS. 5-7, when an endoscopic instrument "I" is inserted into opening 103 of base 102, elongated member 110 unrolls and stretches radially to accommodate instrument "I". Once received within elongated member 110, instrument "I" may be manipulated as desired. The low profile of base 102 and the configuration of elongated member 110 permit instrument "I" to be manipulated to a greater degree than an instrument inserted through a convention access assembly. The internal surface of elongated member 110 and/or the external surface of instrument "I" may be coated with silicone or other suitable substance to facilitate insertion and removal of instrument "I" from within elongated member 110. Removal of instrument "I" causes elongated member 110 to return to the initial, pre-stretched condition wherein the elongated member 110 rolls upon itself to create a seal. Access assembly 100 may be installed using a veress needle or standard obturator.

Figure 8:
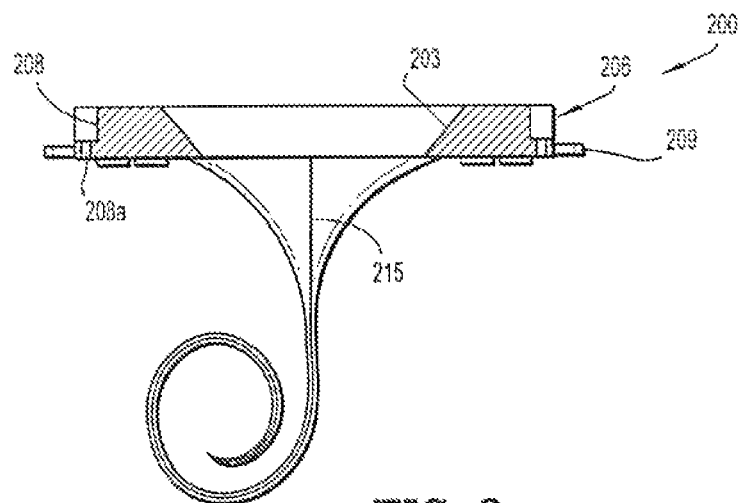
FIG. 8 is a side cross-sectional view of an alternate embodiment of an access assembly according to the present disclosure.
Figure 9:
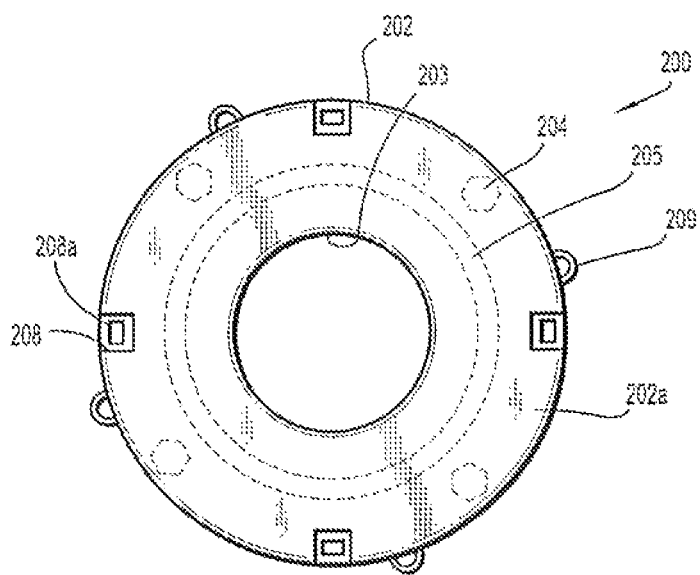
FIG. 9 is a top view of the access assembly of FIG. 8.
Figure 10:
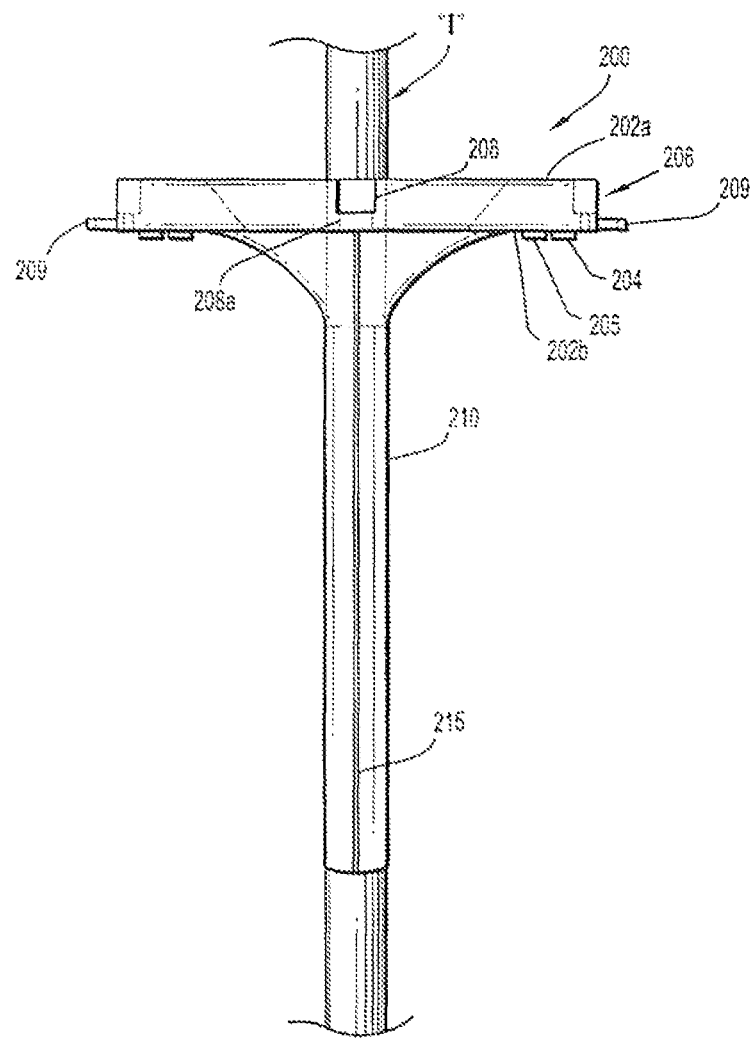
FIG. 10 is side view of the access assembly of FIGS. 8 and 9 illustrating an endoscopic instrument positioned within the access assembly.

Referring now to FIGS. 8-10, an alternate embodiment of an access assembly according to the present disclosure is shown generally as access assembly 200. Access assembly 200 is substantially similar to access assembly 100 described hereinabove, and will only be described as relates to the differences therebetween. Access assembly 200 includes a base 202 and elongated member 210.

With continued reference to FIGS. 8-10, base 202 includes proximal and distal surfaces 202a. 202b and defines opening 203 sized to receive an endoscopic instrument. Opening 203 may includes sloped edges for assisting in receipt of instrument "I" and/or for increasing the range of manipulation of endoscopic instrument "I". Base 202 includes sealing ring 205 mounted on distal surface 202b and about opening 203 for maintaining a seal between the patient and access assembly 200. Base 202 may alternately or further include adhesive pads 204 spaced about distal surface 202b for selectively securing base 202 to a patient. Base 202 further includes suture tie down members 206. Suture tie down members 206 may include recesses 208 and/or tabs 209. Recesses 208 are formed in and extend about the perimeter of base 202 and include openings 208a therein for receiving sutures. In this manner, a surgeon may secure access assembly 200 to a patient utilizing sutures placed through openings 208a in recesses 208. Alternatively, suture tie down members 206 may include tabs 209. Tabs 209 function in a manner similar to recess 208, permitting a surgeon to secure base 202 to a patient with sutures.

With reference to FIGS. 8 and 10, seal member 210 may include one or more support members 215 extending the length thereof. Support member 215 may include a flexible metal wire, plastic strip or other suitable material. Support member 215 is securely attached to elongated member 210 and may alternately be integrally formed therewith. Support member 215 may be configured to roll elongated member 210 upon itself in the absences of endoscopic instrument "I" being inserted therethrough. In this manner, support member 215 ensures that elongated member 210 creates a seal. Support member 215 may further be configured to prevent the inversion of elongated member 210 as endoscopic instrument "I" is removed horn access assembly 200.

Although the illustrative embodiments of the present disclosure have been described herein with reference to the accompanying drawings, it is to be understood, that the disclosure is not limited to those precise embodiments, and that various other changes and modifications may be effected, therein by one skilled in the art without departing from the scope or spirit of the disclosure.

The invention claimed is:

1. A surgical access assembly comprising;
a base defining a longitudinal axis and including an opening formed about the longitudinal axis for receipt of a surgical instrument; and
an elongated member extending from the base and defining a passageway for passage of at least a portion of the surgical instrument, the elongated member including a first, substantially rolled configuration and a second, unrolled configuration, wherein a distal end of the elongated member is closed in the absence of the surgical instrument therethrough when the elongated member is in either of the first configuration or the second configuration.

2. The surgical access assembly of claim 1, wherein the elongated member is rolled about an axis that is transverse to the longitudinal axis when in the first configuration.

3. The surgical access assembly according to claim 1, wherein the elongated member is adapted to establish a substantial sealed relation with the surgical instrument, received within the passageway.

4. The surgical access assembly according to claim 1, wherein the elongated member comprises elastomeric material and is adapted to permit angulated movement of the surgical instrument relative to the central axis.

5. The surgical access assembly of claim 1, wherein the base includes an adhesive ring for selectively sealing the base to a patient.

6. The surgical access assembly of claim 1, wherein the base includes one or more suture tie down members.

7. The surgical access assembly of claim 6, wherein the suture tie down members include recesses formed about the perimeter of the base.

8. The surgical access assembly of claim 6, wherein the suture tie down members include tabs extending from the perimeter of the base.

9. The surgical access assembly of claim 1, wherein the elongated member includes a coating for facilitating the insertion and removal of an endoscopic instrument.

10. The surgical access assembly of claim 1, wherein the elongated member is configured to receive endoscopic instruments of varying/diameters.

11. The surgical access assembly of claim 1, wherein the elongated member is configured to receive an endoscopic instrument having a curved length.

12. The surgical access assembly of claim 1, wherein the base includes a substantially disc-shaped member having a low profile.

13. The surgical access assembly of claim 1, wherein the base is devoid of a seal.

* * * * *